(12) United States Patent
Joshi

(10) Patent No.: US 6,810,288 B2
(45) Date of Patent: Oct. 26, 2004

(54) DEVICE AND METHOD FOR WOUND HEALING AND INFECTION CONTROL

(75) Inventor: Ashok V. Joshi, Salt Lake City, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 119 days.

(21) Appl. No.: 10/096,321

(22) Filed: Mar. 12, 2002

(65) Prior Publication Data

US 2003/0050674 A1 Mar. 13, 2003

Related U.S. Application Data

(60) Provisional application No. 60/303,625, filed on Jul. 6, 2001.

(51) Int. Cl.[7] .................................................. A61N 1/08
(52) U.S. Cl. .......................................... 607/50; 604/25
(58) Field of Search ....................... 604/23, 25; 607/50, 607/88

(56) References Cited

U.S. PATENT DOCUMENTS 5,052,382 A * 10/1991 Wainwright
6,110,431 A * 8/2000 Dunder
6,403,033 B1 * 6/2002 Gutman

FOREIGN PATENT DOCUMENTS

DE 491523 * 2/1930

* cited by examiner

*Primary Examiner*—Mark Bockelman
(74) *Attorney, Agent, or Firm*—Factor & Lake

(57) ABSTRACT

A wound healing device comprising a housing, a corona and/or ultra-violet light generating member ultrasonic wave generator, and/or a photoactivatable material. The housing includes a cavity and at least one opening. The member for generating corona and/or ultra-violet light within the cavity of the housing includes a surface corona discharge device and a power supply associated therewith. The photoactivatable material is positioned within the cavity of the housing. The device further comprises an ultrasonic wave generator and/or oxygen generator within the cavity of the housing.

31 Claims, 3 Drawing Sheets

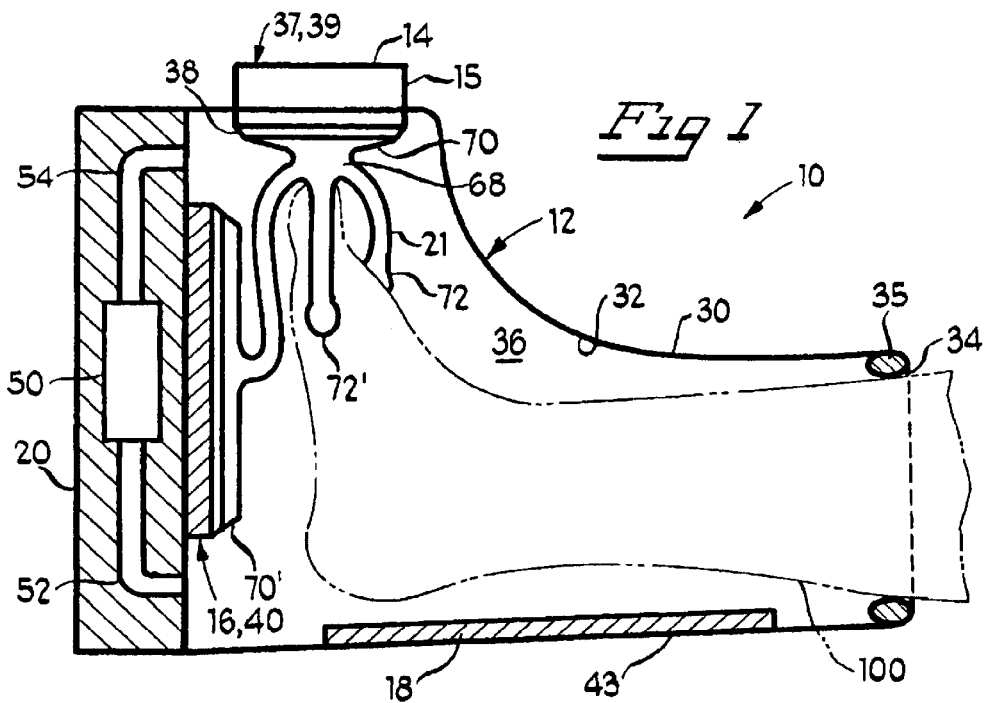
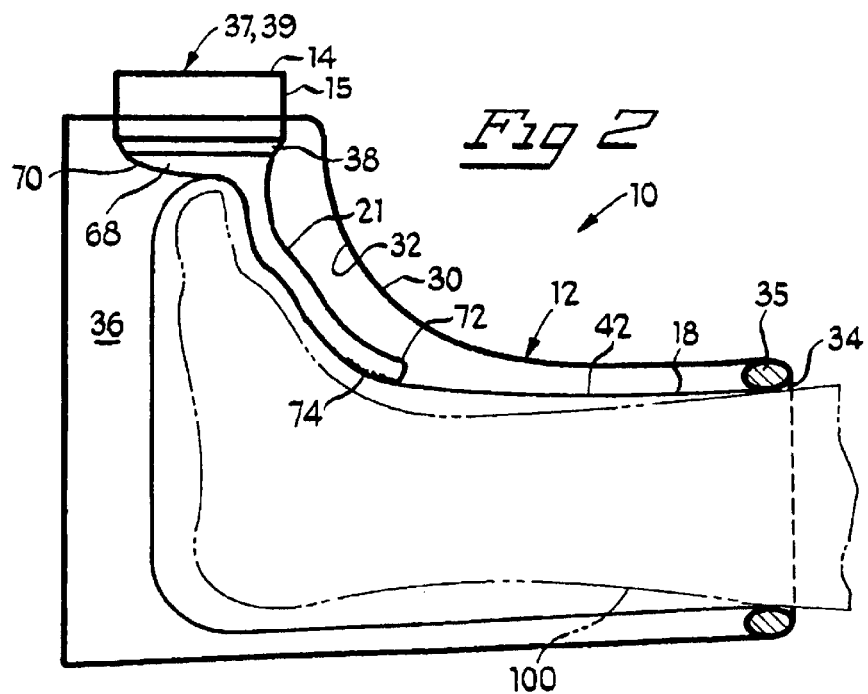

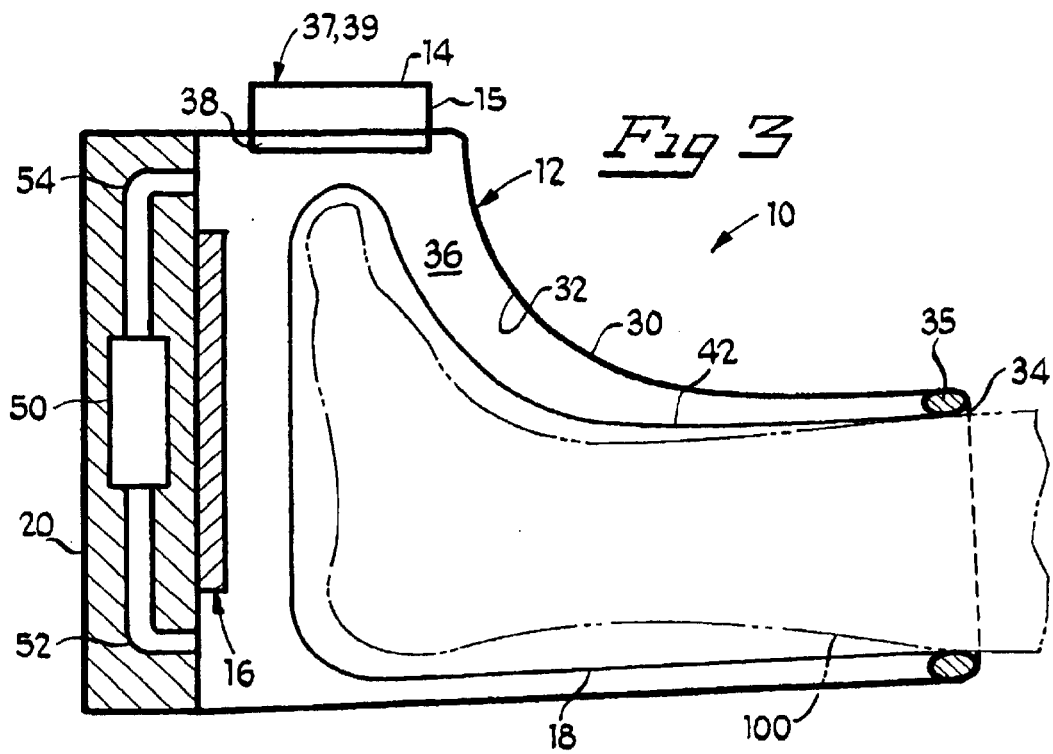
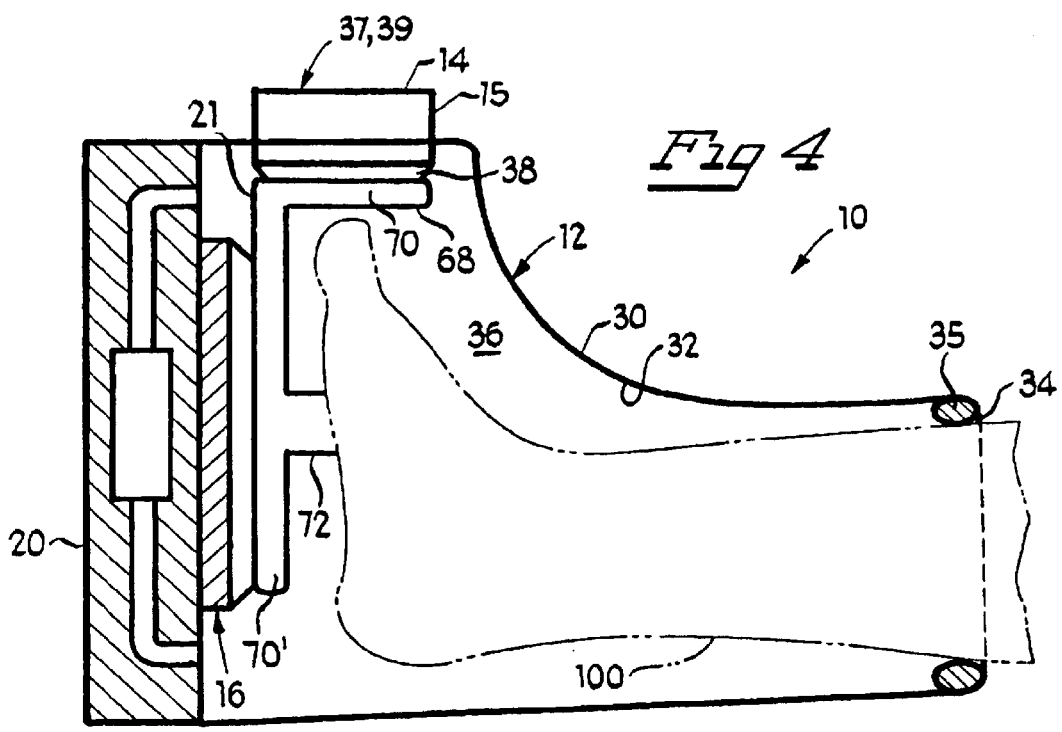

DEVICE AND METHOD FOR WOUND HEALING AND INFECTION CONTROL

The present application is a continuation of a U.S. Provisional Application Ser. No. 60/303,625 filed on Jul. 6, 2001.

BACKGROUND OF THE INVENTION

1. Field of the Invention

The invention relates in general to a device and method for wound healing, including various kinds of wounds such as infectious wounds, burn wounds, diabetic ulcers, post amputation wounds, surgical wounds, etc. The device is intended to kill or neutralize the infectious, microorganisms, germs, bacteria and any undesirable contaminants. The device is also intended, in certain embodiments, to provide a cleaner active oxygen environment to promote the healing of the wound. In certain embodiments, the device incorporates a ceramic surface corona discharge unit as well as photoactive material (reusable and/or discardable), which is associated with the wound. In yet other embodiments, the device incorporates any combination of corona generator, ultrasonic wave generator, ultraviolet light, oxygen generator, $NO_x$ generator and photocatalytic materials. This unique device can be very small and ambulatory.

2. Background Art

Various chemical and medicant methods of treating infectious wounds exist in the literature. Ozone is well known to be used as a bactericidal agent for the inhibition of wounds and for the creation of an improved environment around the wound. There are devices for wound healing, for example, SPM recovery Technologies, Ltd., an Israeli company has developed ozone equipment to treat the infectious wounds. These types of equipment devices are too bulky, non-ambulatory, power intensive and are very costly. Further, these devices would be cumbersome to use at home. They are also difficult to clean after each use.

Thus, it is an object of the invention to provide a wound healing device which is capable of overcoming the above-described deficiencies in the prior art.

SUMMARY OF THE INVENTION

The invention discloses a wound healing device. The device comprises a housing means for generating at least one of corona, ultra-violet light, ultrasonic waves and, a photoactivatable material. The housing includes a cavity and at least one opening. The corona and/or ultra-violet light generating means may include a surface corona discharge device and a power supply associated therewith. The photoactivatable material is positioned within the cavity of the housing. Certain embodiments may omit the use of a photoactivatable material within the cavity (i.e., embodiments which do not have means for generating ultra-violet light). It is also contemplated that the corona generating means generate ions when in contact with air.

In one embodiment, the surface corona discharge device is capable of producing at least one or all of ozone, nitric oxide or ultraviolet light.

In another embodiment, the device further comprises means for circulating fluid within the cavity. In one such embodiment, the fluid circulating means comprises a fan.

In a preferred embodiment which includes a photoactivatable material, which may include a porous bag capable of encircling an area to be treated on a patient. The photoactivatable material may be selected from the group consisting of: photocatalytic materials such as $TiO_2$ and Titanates; $Fe_2O_3$ and compounds of $Fe_2O_3$ and other oxides; Silver and Copper Oxides, halides and chalcogenides; Vanadium pentoxide and vandates; Tin oxides and stannates; $NbO_2$ and Niobates; $TiO_2$ and NbO2 solid solutions; $Bi_2O_3$ and bismuth chalcogenides; Silicon and Germanium doped with p-type and n-type impurities; P-N junctions of semiconductors, such as Si, ZnS, GaAs, etc.; Photovoltaic materials, such as silicon, Ge, InP, ZnP; and Zinc chalcogenides and Zn oxides and Zn phosphides.

In another preferred embodiment, the device further includes means for generating oxygen within the cavity of the housing. In one embodiment, the oxygen generating means comprises at least one of a gas generating cell and a electro-chemical generating cell. Such cells may include metal peroxides having materials containing $ZnO_2$, $CaO_2$, $MgO_2$, AgO, $O_2$, $NaO_2$ and $KO_2$.

In another preferred embodiment, the wound healing device further comprises means for focusing agents generated by the generating means onto a desired region of the cavity. In one embodiment, the focusing means comprises an extension tube. The extension tube includes at least one first end and at least one second end. The at least one first end is associated with the generating means and the at least one second end is positioned proximate a desired application region.

In another preferred embodiment, the wound healing device further comprises means for increasing blood flow to a desired region of the patient. In one embodiment, the blood flow increasing means comprises a $NO_x$ generator. In another embodiment, the blood flow increasing means comprises the surface corona discharge device.

In another preferred embodiment, the wound healing device further comprises means for generating ultrasonic waves within the cavity of the housing.

The invention further comprises a method for treating a wound comprising the steps of providing a housing having a cavity, positioning at least a portion of the wound within a cavity of the housing and one or both of the steps of generating ozone within the cavity of the housing and generating ozone within the cavity. In an embodiment wherein the method includes the step of generating the ultra-violet light, the method further includes the step of associating at least a portion of the wound with a photoactivatable material.

In a preferred embodiment, the method further comprises the step of generating oxygen within the cavity.

In another preferred embodiment, the method further comprises the step of circulating the fluid within the cavity.

In another preferred embodiment, the method further comprises the step of increasing the flow of blood to a desired region.

In another preferred embodiment, the method further comprises the step of focusing the generated constituents onto a desired region.

In still another preferred embodiment, the method further comprises the step of generating ultrasonic waves in the cavity.

BRIEF DESCRIPTION OF THE DRAWINGS

FIG. 1 of the drawings is a cross-sectional view of an embodiment of the present invention;

FIG. 2 of the drawings is a cross-sectional view of an embodiment of the present invention;

FIG. 3 of the drawings is a cross-sectional view of an embodiment of the present invention;

FIG. 4 of the drawings is a cross-sectional view of an embodiment of the present invention FIG. 5 of the drawings is a cross-sectional view of an embodiment of the present invention;

DETAILED DESCRIPTION OF THE DRAWINGS

Figure 5:
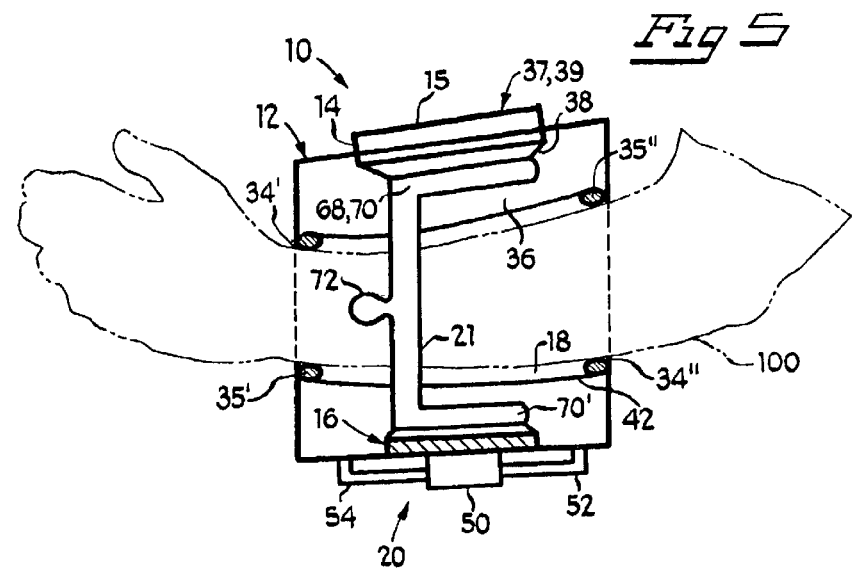

While this invention is susceptible of embodiment in many different forms, there is shown in the drawings and described herein in detail specific embodiments with the understanding that the present disclosure is to be considered as an exemplification of the principles of the invention and is not intended to limit the invention to the embodiments illustrated.

Referring now to the Figures, and in particular to FIG. 1, wound healing and infection control device (hereinafter the device) is shown generally at 10. such a device is particularly useful in association with the healing of surface wounds on patient 100. These wounds may include, but are not limited to, infectious wounds, burn wounds, diabetic ulcers, post amputation wounds, surgical wounds, bed source wounds, etc. Of course, the use of such a device is not limited to these particular wounds, or to wounds in general; rather, the use of such a device is contemplated in a variety of fields.

Device 10, as shown in FIG. 1, comprises housing 12, means 14 for generating at least one of corona and ultra-violet light, means 15 for increasing blood flow, means 16 for generating oxygen, photoactivatable material 18, means 20 for circulating gasses within housing 12 and means 21 for focusing at least one of generating means 14, blood flow increasing means 15 and oxygen generating means 16. It is contemplated that device 10 may be compact and light so as to be substantially ambulatory. In fact, it is contemplated that it may be utilized without immobilizing the user, and, instead permitting the user to proceed with other activities during treatment. Among other embodiments, as shown in FIGS. 7(a)–7(d), it is contemplated that the device may be reduced in size and weight such that similar to socks, gloves, shoes, insoles, etc that a user might normally utilize.

Housing 12 is shown in FIG. 1 as comprising outer surface 30, inner surface 32 and at least one opening, such as opening 34. Inner surface 32 defines cavity 36 with opening 34 providing ingress into cavity 36. Opening 34 may include seal 35 which fits tightly between the housing and the part of the patient which extends through the opening. The seals may be coated with ozone destruction catalyst materials, such as noble metals (Pt, Ru, Au, etc.), high surface area metal oxides ($MnO_2$, $Al_2O_3$, $CuO_2$, etc.) and catalytic carbon powder, among others, to minimize the potential egress of ozone from within cavity 36. Housing 12 may comprise any number of different materials, preferably, such materials are compatible with corona and ultra-violet light that may be generated within the cavity thereof.

Figure 6:
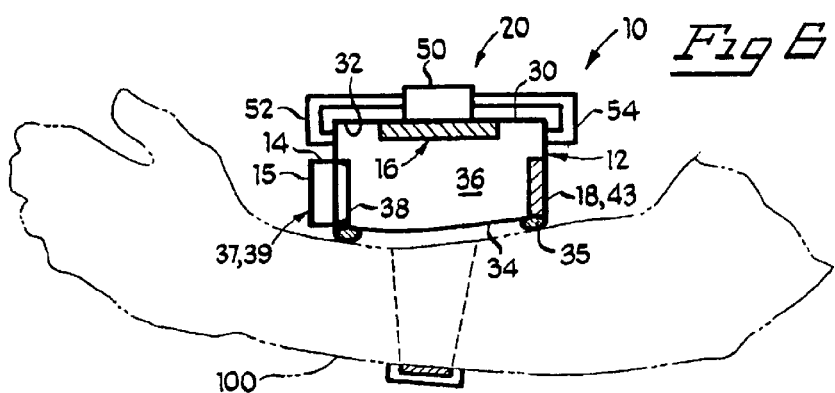
FIG. 6 of the drawings is a cross-sectional view of an embodiment of the present invention.
Figure 7A:
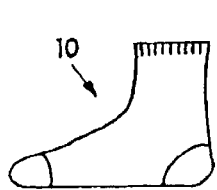
FIGS. 7(a)–7(d) of the drawings is a cross-sectional view of various configurations of the present invention.
Figure 7B:
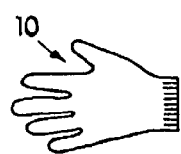
Figure 7C:
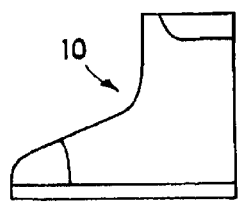
Figure 7D:
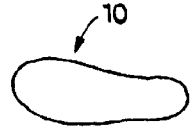

Additionally, it will be understood that housing 12 may comprise any shape and is not limited to any particular shape. Solely by way of example, and not to be limited thereto, housing 12 may be sized and shaped so that cavity 36 is capable of receiving (through opening 34) a leg, a foot, an arm or another body part of a patient. In another embodiment, as shown in FIG. 6, wherein the device 10 is in the form of a patch, wherein the patch housing may comprise a cavity with a larger opening, wherein the opening is positioned to overlie the skin of a patient (such as a bandage or the like). In yet other embodiments, as shown in FIG. 5, the device may include a plurality of openings 34', 34" (having seals 35', 35", respectively).

Corona and/or ultra-violet light generating means 14 is shown in FIG. 1 as comprising surface corona discharge ceramic device 38 associated with control circuit 37 and power supply 39 (i.e., a DC or AC power source). The surface corona discharge ceramic device is electrically connected to power supply 39 and electrically associated with control circuit 37, such that ultra-violet light and corona is generated upon the application of power from the power supply to the surface corona discharge ceramic device. The duration and intensity of the ultra-violet light as well as the duration and quantity of generated corona can be controlled by the control circuit.

The surface corona discharge ceramic device 38 is positioned such that the generated corona and ultra-violet light is directed into cavity 36. Such a surface corona discharge ceramic device produces one or more of ozone, hydroxyl radicals, active oxygen and active catalysts, which kill and neutralize any microbial contaminants surrounding the wound. Preferably, the materials utilized are capable of producing ultra-violet light which has a wavelength generally less than about 400 nm. One such group of surface corona discharge devices is commercially available from NTK under the model numbers ET-OSC60R, ET-OSC37RS, ET-OZC36RS and ET-OSC37RS, among others. Such devices generally convert $O_2$ to $O_3+O_2$ and can produce in the range of 0 to 100 mg of ozone per hour, operate at a discharge frequency from less than about 10 KHz to in excess of 50 KHz. Of course, the production of ozone through such cells is a function of the flow rate of oxygen past the device as well as the oxygen concentration and the relative humidity. Such devices typically likewise produce agents including, but not limited to, photons, $NO_x$, and active oxygen In other embodiments, it is desirable to separate the corona and ultra-violet generating means into two separate components, i.e., a separate corona generator and a separate source of ultra-violet light (e.g. L.E.D. lights). Such embodiments may utilize a first structure for the generation of corona and a simple light source for generating ultra-violet light of the desired wavelength. Of course, materials other than surface corona discharge ceramic devices are contemplated for use which can perform the foregoing functions. The advantage of the surface corona discharge ceramic devices is that they are relatively small devices which can be procured inexpensively and which have relatively small power demands and control requirements. It is likewise desirable to include an ultrasonic wave generator and/or one or more of a photocatalytic means, ultraviolet means, corona generator means and an oxygen generator means.

Blood flow increasing means 15 comprises a $NO_x$ generating device capable of generating predetermined quantities of $NO_x$ into the cavity 36 defined by the housing. Indeed, it has been found that exposure of, for example, a wound to $NO_x$ increases the blood flow therein. In the embodiment shown, the blood flow increasing means comprises the surface corona discharge device, which, produces a predetermined quantity of $NO_x$. In other embodiments, it is contemplated that various other devices can be utilized to create $NO_x$ or to otherwise provide materials which are capable of increasing blood flow proximate the affected area or wound.

In certain embodiments, it may be desirous to utilize only some of the generated agents of the surface corona discharge device. In such an embodiment, the undesirable product can be neutralized (through the use of filters), otherwise vented to the outside or chemically neutralized within the cavity.

Blood flow increasing means 15 comprises a $NO_x$ generating device capable of generating predetermined quantities of $NO_x$ into the cavity 36 defined by the housing. Indeed, it has been found that exposure of, for example, a wound to $NO_x$ increases the blood flow therein. In the embodiment shown, the blood flow increasing means comprises the surface corona discharge device, which, produces a predetermined quantity of $NO_x$. In other embodiments, it is contemplated that various other devices can be utilized to create $NO_x$ or to otherwise provide materials which are capable of increasing blood flow proximate the affected area or wound.

Oxygen generating means 16 is shown in FIG. 1 as comprising a conventionally available chemical and/or electrochemical gas generating cell 40. Chemical and/or electrochemical gas generating cell 40 may comprise any number of different materials which are capable of generating oxygen. For example, the gas generating cell may comprises a material with excess oxygen such as peroxides and oxygen intercalation compounds. These materials react upon contact with water releasing oxygen. Of course, other materials are likewise contemplated for use, including, but not limited to metal peroxides having materials containing $ZnO_2$, $CaO_2$, $MgO_2$, $AgO$, $O_2$, $NaO_2$ and $KO_2$. Of course, the quantity and type of reactants in the chemical gas generating cell and a fixed power supply to electrochemical gas generating cells can control the quantity of oxygen produced and the rate at which the oxygen is produced.

It will be understood that other embodiments may utilize compressed oxygen tanks with adequate control units to meter the release of oxygen from the tanks into the cavity. In yet other embodiments, it is contemplated that other types of oxygen generators can be utilized in place of those identified above.

Photoactivatable material 18 is shown in FIGS. 2, 3 and 5 as being associated with porous bag member 42 positioned within cavity 36 and configured so as to facilitate the receipt of the area to be treated. In other embodiments, as shown in FIG. 1, photoactivatable material 18 may comprise substrate 43 positioned within cavity 36 proximate the area of the patient to be treated. The particular shape of the photoactivatable material can be varied within the scope of the present invention.

The photoactivatable material may be selected from any one of the following constituents (while not being limited thereto):

Photoactivatable Materials $TiO_2$ and Titanates $Fe_2O_3$ and compounds of $Fe_2O_3$ and other oxides Silver and Copper Oxides, halides and chalcogenides Vanadium pentoxide and vandates Tin oxides and stannates $NbO_2$ and Niobates $TiO_2$ and $NbO2$ solid solutions $Bi_2O_3$ and bismuth chalcogenides Silicon and Germanium doped with p-type and n-type impurities P-N junctions of semiconductors, such as Si, ZnS, GaAs, etc.

Photovoltaic materials, such as silicon, Ge, InP, ZnP

Zinc chalcogenides and Zn oxides and Zn phosphides.

In addition, it will be understood that in certain embodiments which do not generate or otherwise utilize ultra-violet light, a photoactivatable and/or photovoltaic material may be omitted from the device.

Circulating means 20 is shown in FIG. 1 as comprising fan 50, inlet duct 52 and exhaust duct 54, which are associated with cavity 36. Fan 50 is shown in FIG. 1 as comprising an electric fan having a desired CFM rating. Inlet duct 52 places cavity 36 in fluid communication with the inlet of the fan and outlet duct 54 places cavity 36 in fluid communication with the outlet of the fan. In various embodiments, it is contemplated that the circulating means may include additional external filters and other members to facilitate the circulation of fluid within the cavity. In addition, certain embodiments (FIG. 2) are contemplated which do not include any type of circulating means.

Focusing means 21 is shown in FIG. 1 as comprising extension tube 68 associated, at first end 70, with at least one of generating means 14, blood flow increasing means 15 and oxygen generating means 16, and associated, at second end 72, with the area to be treated. In certain embodiments it is contemplated that focusing means 21 may include a plurality of first ends 70, 70', etc., as well as a plurality of second ends 72, 72', etc. Specifically, the extension tube is capable of directing the agents produced by the above-identified means directly to the affected area or to another desired area (i.e., directing UV light to particular portions of the photoactivatable material). In certain embodiments, the extension tube may comprise a material which is user deformable into a desired shape. In other embodiments, second end 72 may include means 74 for releasably attaching the second end proximate the desired area. Releasable attachment means 74 may comprise any one of an adhesive, an belt member, tape, among others.

In operation, the location of the particular wound to be treated is designated (i.e., the surface area that is to be treated). The application will be described with respect to an infectious wound on the leg of a patient. Once the particular wound region is determined, an appropriately sized device is associated with the wound that is to be treated. In one particular case, a suitable device is shown in FIG. 3 as encapsulating the leg from approximately the knee downward within the housing. Of course, the invention is not limited to any particular configuration of the device and variously sized and shaped devices are contemplated for use. Advantageously, however, due to the relatively small size and power requirements of the above-identified components, it is contemplated that such devices may be ambulatory and may be conveniently be carried by the patient for use when desired.

Once the device is selected, the patient's leg is inserted into cavity 36 through opening 34 into porous bag member 42, and positioned in an orientation which is comfortable to the user. Next, the surface corona discharge device is activated so as to provide ultra-violet light and corona into cavity 36. The ultra-violet light activates the photoactive material, which, in turn, kills and neutralizes microorganisms proximate to the photoactive material. In addition, the corona generated by the surface corona discharge device further disinfects the portion of the patient's body that is within the cavity (including the wound area). The duration and intensity of generation of corona and the generation of ultra-violet light is controlled by control circuitry 37.

The oxygen generating means is likewise activated so as to generate oxygen within cavity 36. The oxygen mixes within the cavity with corona, which has been shown to have a synergistic effect on the healing of wounds. Of course, certain embodiments may (FIG. 2) omit the use of an oxygen generating means (i.e., embodiments which have size considerations and power considerations). As explained above, the oxygen generating means can be designed to generate a particular quantity of oxygen over a predetermined period of time.

In embodiments that include focusing means 21, the focusing means are utilized to direct the produced agents to the desired area. In particular, prior to activation of the various means, the extension tube of the focusing means can be manipulated so that the second end thereof is positioned in a desired spatial orientation proximate the desired area. In this manner, the agents produced by the various means can be directly focused onto the desired area.

Once the corona and oxygen are being generated, fluid circulating means can be activated. In such an embodiment having fluid circulating means, the circulating means can circulate the oxygen and corona throughout the cavity so as to enhance the exposure of such materials to the wound that is to be treated.

The treatment can continue for a predetermined period of time. For example, it is contemplated that the control circuitry 37 can control the treatments such that the treatments may be for between 15 minutes and 4 hours at a time. In other embodiments, it is contemplated that the treatments may be cyclical in nature, wherein control circuit 37 cycles the device off and on for predetermined periods of time.

Certain tests were conducted relative to the efficacy of the foregoing device relative to the killing and neutralizing any microbial contaminants surrounding the wound. Specifically, the device, and, more particularly, the corona discharge device of the present invention was evaluated by inoculating the surface of glass slides with cultures of clinically relevant microorganisms including: methicillin resistant *Staphylococcus aureus* (MRSA, ATCC #700698), vancomycin resistant *Enterococcus faecium* (VRE, ATCC #700221), *Pseudomonas aeruginosa* (ATCC #15442), *Streptococcus pneumoniae* (Strep B, ATCC #29514), *Salmonella choleraesuis* (ATCC #10708), *Bacillus subtilus* spores (ATCC #9372), *Clostridium sporogenes* spores (ATCC #3584), *Mycobacterium bovis* BCG (TB, ATCC #35743), *Candida albicans* (yeast, ATCC #10231) and *Aspergillus niger* (fungus, ATCC #16404). The unit was turned on for specified time intervals, and then the organisms were extracted using standard bioburden procedures after exposure to evaluate organism reduction. Unexposed positive controls gave the starting titers for the test organisms.

The unit was placed in a fully exhausted HEPA filtered hood. Glass slides of each type of organism were placed, in triplicate, into the unit, which comprised an airtight container with dimensions of 10×12×5 inches and equipped with a miniature corona generator. The device was activated at ambient temperature. Slides with *S. aureus, E. faecium, P. aeruginosa, S. pneumoniae,* and *S. choleraesuis* were exposed for 30 minutes, one hour, or two hours. Slides with *B. subtilis, C. sporogenes, M. bovis, C. albicans* and *A. niger* were exposed for one hour, four hours, or sixteen hours.

Results

Test data for several examples are reported in the Table below. As can be seen, very high levels of efficacy were achieved with these recalcitrant, pathogenic organisms.

TABLE

| Sample ID | | Control Titer | % Reduction | Log Reduction |
|---|---|---|---|---|
| 30' Exposure | #1 | $3.3 \times 10^6$ CFU/slide | 97.03% | 1.53 |
| *P. aeruginosa* | #2 | $3.3 \times 10^6$ CFU/slide | 98.61% | 1.86 |
| | #3 | $3.3 \times 10^6$ CFU/slide | 98.42% | 1.80 |
| 60' Exposure | #1 | $3.3 \times 10^6$ CFU/slide | 98.42% | 1.80 |
| *P. aeruginosa* | #2 | $3.3 \times 10^6$ CFU/slide | 99.85% | 2.82 |
| | #3 | $3.3 \times 10^6$ CFU/slide | 98.70% | 1.89 |
| 120' Exposure | #1 | $3.3 \times 10^6$ CFU/slide | 99.15% | 2.07 |
| *P. aeruginosa* | #2 | $3.3 \times 10^6$ CFU/slide | 99.36% | 2.20 |
| | #3 | $3.3 \times 10^6$ CFU/slide | 98.58% | 1.85 |
| 30' Exposure | #1 | $6.6 \times 10^6$ CFU/slide | 97.88% | 1.67 |
| *S. choleraesuis* | #2 | $6.6 \times 10^6$ CFU/slide | 96.52% | 1.46 |
| | #3 | $6.6 \times 10^6$ CFU/slide | 98.70% | 1.89 |
| 60' Exposure | #1 | $6.6 \times 10^6$ CFU/slide | 99.02% | 2.01 |
| *S. choleraesuis* | #2 | $6.6 \times 10^6$ CFU/slide | 98.82% | 1.93 |
| | #3 | $6.6 \times 10^6$ CFU/slide | 98.52% | 1.83 |
| 120' Exposure | #1 | $6.6 \times 10^6$ CFU/slide | 99.70% | 2.52 |
| *S. choleraesuis* | #2 | $6.6 \times 10^6$ CFU/slide | 99.71% | 2.54 |
| | #3 | $6.6 \times 10^6$ CFU/slide | 99.80% | 2.71 |
| 30' Exposure | #1 | $2.2 \times 10^6$ CFU/slide | 93.2% | 1.17 |
| MRSA | #2 | $2.2 \times 10^6$ CFU/slide | 92.3% | 1.11 |
| | #3 | $2.2 \times 10^6$ CFU/slide | 91.4% | 1.06 |
| 60' Exposure | #1 | $2.2 \times 10^6$ CFU/slide | 94.5% | 1.26 |
| MRSA | #2 | $2.2 \times 10^6$ CFU/slide | 95.0% | 1.30 |
| | #3 | $2.2 \times 10^6$ CFU/slide | 96.0% | 1.40 |
| 120' Exposure | #1 | $2.2 \times 10^6$ CFU/slide | 95.0% | 1.30 |
| MRSA | #2 | $2.2 \times 10^6$ CFU/slide | 96.2% | 1.42 |
| | #3 | $2.2 \times 10^6$ CFU/slide | 97.3% | 1.57 |
| 60' Exposure | #1 | $3.1 \times 10^6$ CFU/slide | 87.74% | 0.91 |
| *B. subtilis* | #2 | $3.1 \times 10^6$ CFU/slide | 86.13% | 0.86 |
| | #3 | $3.1 \times 10^6$ CFU/slide | 92.90% | 1.15 |
| 4 Hr Exposure | #1 | $3.1 \times 10^6$ CFU/slide | 99.26% | 2.13 |
| *B. subtilis* | #2 | $3.1 \times 10^6$ CFU/slide | 99.35% | 2.19 |
| | #3 | $3.1 \times 10^6$ CFU/slide | 99.19% | 2.09 |
| 16 Hr Exposure | #1 | $3.1 \times 10^6$ CFU/slide | 99.98% | 3.76 |
| *B. subtilis* | #2 | $3.1 \times 10^6$ CFU/slide | 99.998% | 4.62 |
| | #3 | $3.1 \times 10^6$ CFU/slide | 99.99% | 3.86 |

Once the treatment is complete, the user can remove the device and either reuse the device, reuse portions of the device or discard the device. In certain embodiments wherein it is contemplated that the device may be reusable, the device can be cleaned for a subsequent use. Further, in reusable devices, components which have been spent, broken or worn (i.e., corona discharge devices, photoactivatable materials, oxygen generators, power supplies) can be replaced with new components. It is specifically contemplated that the photoactivatable material is replaced after each use. In one embodiment, wherein the photoactivatable material is associated with a porous bag, the entire porous bag may be replaced after each use.

In other embodiments, wherein the devices may be disposable, the devices are merely discarded after use. Such contemplated devices include, but are not limited to, a glove, a shoe insole or a specialized sock. With these type of devices, the patient can operate the device and receive the proper treatment substantially discretely and while undertaking other activities. In addition, after treatment, the user can discard the device. Indeed, multiple disposable devices can be provided to a patient, to, in turn, provide a full treatment plan which consists of a plurality of individual treatments with each disposable device over a predetermined period of time.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A disposable wound healing device comprising:
    a patch having a housing with at least one cavity, and at least one opening, wherein the cavity is adapted to at least partially surround a wound region of a patient; and
    a surface corona discharge device integral within the cavity and adapted to be positioned proximate the wound, wherein the surface corona discharge device generates a corona discharge towards the wound, and within the cavity.

2. The would healing device of claim 1 wherein the corona generating means generates ions when in contact with air.

3. The wound healing device of claim 1 wherein the corona generating means further comprises:
    control circuitry associated with the surface corona discharge device, to, in turn, control the generation of corona.

4. The wound healing device of claim 1 wherein the surface corona discharge device is capable of producing up to about 100 mg of ozone per hour.

5. The wound healing device of claim 1 further comprising means for circulating fluid within the cavity.

6. The wound healing device of claim 5 wherein the fluid circulating means comprises a fan.

7. The wound healing device of claim 1 wherein the corona generating means generates ultra-violet light, the device further comprising a photoactivatable material positioned within the cavity of the housing.

8. The wound healing device of claim 7 wherein the photoactivatable material is associated with at least one of a porous bag capable of encircling an area to be treated on a patient and a substrate associated with the cavity.

9. The wound healing device of claim 7 wherein the photoactivatable material is selected from the group consisting of: $TiO_2$ and Titanates; $Fe_2O_3$ and compounds of $Fe_2O_3$ and other oxides; Silver and Copper Oxides, halides and chalcogenides; Vanadium pentoxide and vandates; Tin oxides and stannates; $NbO_2$ and Niobates; $TiO_2$ and NbO2 solid solutions; $Bi_2O_3$ and bismuth chalcogenides; Silicon and Germanium doped with p-type and n-type impurities; P-N junctions of semiconductors, such as Si, ZnS, GaAs, etc.; Photovoltaic materials, such as silicon, Ge, InP, ZnP; and Zinc chalcogenides and Zn oxides and Zn phosphides.

10. The wound healing device of claim 7 wherein the photoactivatable material is at least one of disposable and replaceable.

11. The wound healing device of claim 1 further comprising means for generating at least one of oxygen, or ultrasonic waves within the cavity of the housing.

12. The wound healing device of claim 11 wherein the oxygen generating means comprises at least one of a gas generating cell and an electrochemical gas generating cell.

13. The wound healing device of claim 12 wherein the oxygen generating means is selected from the group consisting of: metal peroxides having materials containing $ZnO_2$, $CaO_2$, $MgO_2$, $AgO$, $O_2$, $NaO_2$ and $KO_2$.

14. The wound healing device of claim 1 further comprising means for focusing the corona generated by the corona generating means onto a desired region of the cavity.

15. The wound healing device of claim 14 wherein the focusing means comprises:
    an extension tube having at least one first end and at least one second end, the at least one first end associated with ozone generating means and the at least one second end positioned proximate a desired application region.

16. The wound healing device of claim 1 further comprising means for increasing blood flow to a desired region of the patient.

17. The wound healing device of claim 16 wherein the blood flow increasing means comprises a $NO_x$ generator.

18. A wound healing device comprising:
    a housing including a cavity and at least one opening;
    means for generating ozone and ultra-violet light within the cavity of the housing, wherein the generating means comprises:
        a surface corona discharge device; and
        a power supply associated therewith; and
        a photoactivatable material positioned within the cavity of the housing.

19. The wound healing device of claim 18 wherein the surface corona discharge device is capable of generating up to about 100 mg of ozone per hour.

20. The wound healing device of claim 18 further comprising means for circulating fluid within the cavity.

21. The wound healing device of claim 20 wherein the fluid circulating means comprises a fan.

22. The wound healing device of claim 18 wherein the photoactivatable material comprises a porous bag capable of encircling an area to be treated on a patient.

23. The wound healing device of claim 18 wherein the photoactivatable material is selected from the group consisting of: $TiO_2$ and Titanates; $Fe_2O_3$ and compounds of $Fe_2O_3$ and other oxides; Silver and Copper Oxides, halides and chalcogenides; Vanadium pentoxide and vandates; Tin oxides and stannates; $NbO_2$ and Niobates; $TiO_2$ and NbO2 solid solutions; $Bi_2O_3$ and bismuth chalcogenides; Silicon and Germanium doped with p-type and n-type impurities; P-N junctions of semiconductors, such as Si, ZnS, GaAs, etc.; Photovoltaic materials, such as silicon, Ge, InP, ZnP; and Zinc chalcogenides and Zn oxides and Zn phosphides.

24. The wound healing device of claim 18 further comprising means for generating oxygen within the cavity of the housing.

25. The wound healing device of claim 24 wherein the oxygen generating means comprises at least one of a gas generating cell and an electrochemical gas generating cell.

26. The wound healing device of claim 25 wherein the oxygen generating means is selected from the group consisting of: metal peroxides having materials containing $ZnO_2$, $CaO_2$, $MgO_2$, $AgO$, $O_2$, $NaO_2$ and $KO_2$.

27. The wound healing device of claim 18 further comprising means for focusing agents generated by the generating means onto a desired region of the cavity.

28. The wound healing device of claim 27 wherein the focusing means comprises:

an extension tube having at least one first end and at least one second end, the at least one first end associated with the generating means and the at least one second end positioned proximate a desired application region.

29. The wound healing device of claim 18 further comprising means for increasing blood flow to a desired region of the patient.

30. The wound healing device of claim 29 wherein the blood flow increasing means comprises a $NO_x$ generator.

31. The wound healing device of claim 29 wherein the blood flow increasing means comprises the surface corona discharge device.

* * * * *